United States Patent

Lucas et al.

Patent Number: 5,449,474
Date of Patent: Sep. 12, 1995

[54] LOW TOXICITY SOLVENT COMPOSITION

[75] Inventors: Joseph A. Lucas, Kent; Zeljko E. Halar, Tacoma, both of Wash.

[73] Assignee: Inland Technology, Inc., Tacoma, Wash.

[21] Appl. No.: 109,693

[22] Filed: Aug. 20, 1993

Related U.S. Application Data

[63] Continuation of Ser. No. 839,854, Feb. 21, 1992, abandoned.

[51] Int. Cl.$^6$ .......... C09D 9/00; C11D 7/26; C11D 7/50; C23G 5/032
[52] U.S. Cl. .......... 252/170; 134/38; 134/40; 252/162; 252/174.21; 252/364; 252/DIG. 8
[58] Field of Search .......... 252/162, 170, 171, 174.21, 252/364, DIG. 8; 134/38, 40

[56] References Cited

U.S. PATENT DOCUMENTS

| | | | |
|---|---|---|---|
| 2,935,479 | 5/1960 | Oberdorfer, Jr. | 252/170 |
| 3,382,181 | 5/1968 | Oberdorfer, Jr. | 252/170 |
| 4,414,128 | 11/1983 | Goffinet | 252/111 |
| 4,435,305 | 3/1984 | Tsoukalas et al. | 252/158 |
| 4,508,634 | 4/1985 | Elepano et al. | 252/163 |
| 4,511,488 | 4/1985 | Matta | 252/162 |
| 4,533,487 | 8/1985 | Jones | 252/170 |
| 4,620,937 | 11/1986 | Dellutri | 252/143 |
| 4,680,133 | 7/1987 | Ward | 252/153 |
| 4,780,235 | 10/1988 | Jackson | 252/170 |
| 4,968,447 | 11/1990 | Dixon et al. | 252/174.23 |
| 4,983,224 | 1/1991 | Mombrun et al. | 134/40 |
| 5,007,969 | 4/1991 | Doscher | 134/38 |
| 5,024,780 | 6/1991 | Leys | 252/162 |
| 5,035,826 | 7/1991 | Durbut et al. | 252/121 |
| 5,039,441 | 8/1991 | Thomas et al. | 252/142 |
| 5,064,557 | 11/1991 | Fusiak | 252/162 |
| 5,078,897 | 1/1992 | McCain | 252/170 |
| 5,098,591 | 3/1992 | Stevens | 252/162 |
| 5,098,594 | 3/1992 | Doscher | 252/162 |
| 5,108,643 | 4/1992 | Loth et al. | 252/174.11 |
| 5,124,062 | 6/1992 | Stevens | 252/162 |
| 5,204,026 | 4/1993 | Doscher-Good | 252/542 |
| 5,236,614 | 8/1993 | Jacquet et al. | 252/96 |

FOREIGN PATENT DOCUMENTS 9100893  1/1991  WIPO .

OTHER PUBLICATIONS

*Grant & Hackh's Chemical Dictionary*, 5th edition, ed by Grant et al 1987 p. 340.

Primary Examiner—Linda Therkorn Skaling
Attorney, Agent, or Firm—Hughes, Multer & Schacht

[57] ABSTRACT

A low-toxicity solvent composition having broad-spectrum applicability. A polar solvent component is provided by an alicyclic carbonate and a non-polar solvent component is provided by a terpene, with a short-chained non-ionic surfactant being provided for coupling the alicyclic carbonate and terpene in a homogeneous, single-phase solution. The composition may be 25–60% propylene carbonate, 1% (or less)–20% d-limonene, and 40–60% tripropylene glycol methyl ether. This solvent composition is non-toxic to personnel, and presents minimal environment hazards. Among its many applications are paint equipment clean-up, cleaning and reclamation of silkscreens, cleaning of offset printing rollers, cleaning of aluma-printing surfaces and equipment, as well as general purpose clean-up of greases, oils, paints, inks, and so forth.

3 Claims, No Drawings

LOW TOXICITY SOLVENT COMPOSITION

This is a continuation of copending application Ser. No. 07/839,854 filed on Feb. 21, 1992, now abandoned.

BACKGROUND OF THE INVENTION

1. Field of the Invention

The present invention relates generally to liquid organic solvents, and more particularly, to such a solvent which effectively dissolves and removes a wide range of materials, yet which is also comparatively non-hazardous to the environment and personnel.

2. Background

Liquid solvent compositions are widely used throughout modern industry. Just a few of the many applications for such solvent compositions include the following processes: oil and grease removal; cleaning of paint guns and lines; stripping paint; washing paint rollers; cleaning and reclamation of silk screens; alumaprinting; deglazing, ink removal, and roller washing in printing processes; lacquer washing.

As is well known to those skilled in the art, the many various materials which must be solubilized in these applications differ greatly in how effectively they can be dissolved by different solvent materials. For example, the materials may be characterized as "polar" or "non-polar" (or somewhere in between) as a result of their molecular structure; it has been found that as a general rule, "like dissolves like", so that materials having a generally polar character will tend to be most effectively solubilized by solvents also having a polar character (i.e., those solvents which rely largely on their electrical dipole characteristics for their solvent action), while materials of a non-polar character are usually more effectively solubilized by solvents which also have non-polar characteristics (i.e., those solvents which work primarily on the basis of their dispersion forces).

While it would thus in some respects be "ideal" to mate the material which is sought to be removed with a solvent which is matched to it in terms of its polar/non-polar characteristics, this is frequently not possible, or is at least impractical. For one thing, coatings and other materials may themselves be made up of both polar and non-polar constituents, and it is necessary for the solvent to be able to act on both of these in order to successfully remove the material. Furthermore, it is simply desirable from an economic and convenience standpoint to have a "general purpose" solvent available which can be relied on to perform many different cleaning tasks involving a wide variety of materials.

Unfortunately, relatively few solvents formulations have been found which are capable cleaning up a broad spectrum of materials having the varied characters discussed above. In general, the search for such general purpose solvents has focused on compounds which exhibit both polar and non-polar characteristics in a single molecule; for example, some molecules are essentially "polar" at one end, and "non-polar" at the other, in terms of their solvent characteristics. Some of these materials (e.g., fatty acids and the like, which are used in detergent mixtures) are characterized by a long-chained molecular structure, and are generally unsuitable for use in many industrial applications, due to the excessive residue which they leave behind, and the amount of rinsing or other secondary washing which is necessary to remove this.

On the other hand, a handful of organic compounds have been identified which have been successfully used as broad spectrum solvents in high technology industries, such as the aerospace and electronic industries, as well as in more commonplace applications. Unfortunately, the great majority of these have ultimately been found to present undesirable toxicologies and serious hazards to the environment; examples of these compounds include methylene chloride and methyl ethyl ketone (MEK), as well as toluene, xylene, and other aromatics, may of which include the additional hazard of high flammability. For example, although MEK has long been considered a satisfactory solvent from the standpoint of cleaning effectiveness, there is a growing concern that the toxicity and flammability of MEK exposes users to unnecessary risks. Also, because used MEK is considered a threat to the environment, and so is classified as a hazardous waste, the expense associated with the safe disposal of MEK is on the order of 5–10 times greater than the amount which the user initially pays for the solvent. Moreover, because of its relatively high vapor pressure, the lose of MEK to the atmosphere during use is excessive, necessitating the use of large and expensive collection systems such as vacuum hoods.

Because of the concern for the safety, health, and environmental hazards which these known organic solvents thus present, both the federal and state governments are promulgating increasingly stringent criteria which solvent users must comply with. For instance, the California State Legislature limits the use of volatile solvents by requiring that they have a vapor pressure below about 45 mmHg at 20° C. In addition, regulations require that solvents be disposed of in a manner that will not adversely effect the environment; for may users of such solvents, this disposal generally translates into increased operating costs, as noted above.

For the above reasons, a primary consideration for many users of organic solvents has become the toxicity of a particular solvent mixture, and also the hazards which it presents to the environment. This has lead to a number of attempts to find safe substitutes for the hazardous organic solvents which have been used in the past. As an example, methylene chloride has been widely used in industry, especially for formulating paint strippers, lacquer removers, and paint clean-up systems, but it suffers from high volatility which leads to excessive evaporation, contributing to worker exposure and environmental pollution. Attempts have consequently been made to replace methylene chloride using various, safer organic solvents, but for the most part these efforts have not yielded solvent compositions which are sufficiently effective or quick in action to gain acceptance, and, furthermore, many of the proposed substitutes have proven to costly to be economically feasible. For example, n-methyl-pyrrolidone (NMP) has sometimes been found to be a suitable substitute for MEK or methylene chloride in terms of its solvent abilities, and it exhibits a very low volatility which drastically reduces the flammability hazard and evaporative losses. However, both the cost of NMP renders it use prohibitive in the concentrations which are necessary to make many of the proposed formulations perform effectively as solvents. Furthermore, NMP is excessively harsh for many applications, in that it will cause damage to the underlying substrate; for example NMP can cause severe deterioration of rubber and plastics, such as PVC.

It also tends to cause irritation and defatting of user's hands.

Accordingly, a need exists for a substantially non-toxic solvent composition which exhibits superior cleaning ability when applied to a variety of substances, and which exhibits low flammability and relatively low vapor pressure so as to limit evaporative losses. Furthermore, there is a need for such a solvent which safely degrades in the environment and in biological systems, and which is also sufficiently inexpensive to be economical for large scale use.

SUMMARY OF THE INVENTION

The present invention has solved the problems cited above and is a low toxicity solvent composition, this comprising broadly (a) an alicyclic carbonate for providing the composition with a polar solvent component; (b) a terpene for providing the composition with a non-polar solvent component; and (c) a short-chained, non-ionic surfactant for coupling the alicyclic carbonate and the terpene in a homogeneous, single-phase solution.

The alicyclic carbonate may be selected from the group consisting of propylene carbonate and ethylene carbonate, and is most preferably propylene carbonate. The propylene carbonate may be present in the composition in an amount from about 25% to about 60% by weight.

The terpene which is used in the composition may be a monoterpene, and this may be selected from the group consisting of d-limonene and l-limonene, with d-limonene being preferred. The d-limonene may be present in an amount from about 1% or less to about 20% by weight.

The short-chained non-ionic surfactant may be a glycol ether. This may be a glycol ether which is selected from the group consisting of propylene-based and ethylene-based glycol ethers, with the propylene-based glycol ethers being preferred. Tripropylene glycol methyl ether is most preferred, and this may be present in the composition in an amount from about 40% to about 60% by weight.

DETAILED DESCRIPTION OF THE INVENTION

As an overview, it has been found that a particularly effective liquid solvent is provided when a liquid mixture of an alicyclic carbonate and a terpene is formed, this being stabilized in a single phase solution by a small-chained, non-ionic surfactant, such as a glycol ether. For example, it has been found that a preferred mixture of propylene carbonate, d-limonene, and tripropylene glycol methyl ether provides a liquid solvent which exhibits superior cleaning properties with respect to a wide variety of materials, a virtual absence of toxicity, and a low vapor pressure which greatly reduces evaporative loss and personnel exposure in use. Furthermore, this mixture is economical to produce, which advantage is enhanced by the fact that the stability of the mixture and the low evaporative loss greatly extends the service life of a given amount of this solvent.

As was noted above, a known (but extremely hazardous) organic solvent which has the ability to solubilize a wide range of materials is methyl ethyl ketone, and this ability is believed to stem from the fact that MEK combines both polar and non-polar characteristics in a single molecule. The present invention, in turn, is intended to produce a solvent material which, on a macro scale, may mimic some of the permanent electrochemical characteristics which are exhibited by MEK in a single molecule. Accordingly, the cyclic carbonate provides the polar component of the solution, and the terpene provides the non-polar component. The glycol ether, in turn, serves as a "coupling agent" which maintains the two solvent portions (i.e., the polar and non-polar portions) in a homogeneous, single phase solution; this enables the solvent system to develop a synergism which permits it to solubilize materials having solvent-related characteristics which lie either at or between these extremes in terms of polarity. The net result is that this composition has been found to exhibit a solvent ability which out-performs any of the three components used separately; this increase in performance has been observed with respect to numerous different materials, and especially with respect to solvent-based paints.

As was noted above, the polar portion of the solvent composition is provided by the alicyclic carbonate compound, these compounds being of the formula:

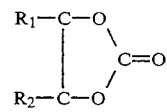

wherein $R_1$ and $R_2$ are selected from the group consisting of hydrogen, methyl, or ethyl. Examples of alicyclic carbonate compounds having this formula which are preferred for use in the composition of the present invention include propylene carbonate and ethylene carbonate. As is known to those skilled in the art, the polar character of those carbonate compounds stems from the strong positive polarity which the oxygen bonding imparts to the carbonate end of the molecule.

The reasons the alicyclic carbonate compounds have been found advantageous for use in the composition of the present invention appear to be at least twofold. Firstly, the cyclic structure of these compounds renders the molecules significantly more compact than their straight-chained equivalents, and this greatly reduces steric (mechanical) hindrances between the molecules of the solvent composition and those of the material which is sought to be solubilized. For example, the compact nature of the cyclic versions of the carbonates appears to make it much easier for those to penetrate the micro-pore structure which exists at the solvent interface with coatings of paint. Secondly, it has been found that these cyclic carbonates are much more readily maintained in a homogeneous, single phase solution with the cyclic terpenes which are the preferred non-polar component of the composition, when these are combined with the glycol ether coupling agent, this apparently being due to "stacking" of the cyclic structures of the carbonate and the terpene in the solution.

Of the two preferred cyclic carbonates noted above, the propylene carbonate is most preferred in the solvent composition of the present invention, in that, while both ethylene and propylene carbonate degrade quickly and safely in the environment, and both exhibit desirably low vapor pressures (as will be discussed further below), the propylene carbonate is considerably safer from the standpoint of personnel exposure, inasmuch as it degrades to safe intermediates and end products within the human metabolic system, while this is not true of ethylene carbonate. In fact, the safety of propylene carbonate is attested to by the fact that it has been widely used is cosmetics. Propylene carbonate suitable for use in the composition of the present invention is available from several sources; for example, Texaco Chemical Company, Thousand Oaks, Calif., supplied suitable propylene carbonate under the brand name TEXACAR*PC ™.

Turning now to the non-polar constituent of the composition, this (as was noted above) is provided by a suitable terpene. As is known to those skilled in the art, such non-polar solvents generally rely more on their dispersion forces for their solvent action, rather than on electrical dipole characteristics, as is the case with the polar compounds.

Terpenes are hydrocarbons often found in essential oils, resins, and other vegetable aromatic products, and, in general, are perceived to be polymers of a 5-carbon moiety referred to as an isoprene unit. Related to the terpenes are the hemiterpenes ($C_5H_8$), sesquiterpenes ($C_{15}H_{24}$), diterpenes ($C_{20}H_{32}$), and the polyterpenes ($n(C_{10}H_{16})$). The monoterpenes ($C_{10}H_{16}$) which are preferred for use in the solvent composition of the present invention are primarily of plant origin, a very large number of these having been isolated and characterized; many have long been used in perfumes and medicines, and consequently many of these present significant advantages in terms of safety for personnel exposure. Examples of suitable terpenes include the di-pentenes d-limonene and l-limonene, and also pinene, terpinene, and terpinolene.

As was noted above, the cyclic terpenes are generally preferred for use in the solvent composition of the present invention, due to their compact molecular structure and ability to "stack" with the cyclic carbonate component of the solution, the most preferable of these being d-limonene, a by-product of the citrus industry; it is also believed that the double-bonded structure of d-limonene provides a flatter ring configuration which more effectively emulates the solvent characteristics of the aromatic hydrocarbons which are sought to be replaced. This compound is derived in various amounts from the rinds or peels of oranges, grapefruits, and other citrus fruits; it safely biodegrades in the environment, and does not present a personnel hazard in terms of exposure, this material having in fact been used in various food products. The structure for d-limonene is given below:

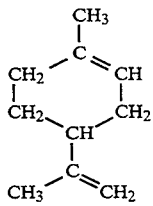

An extensive discussion of d-limonene, and its derivation from various sources, is presented in a book by J. W. Kesterson, R. Hendrickson, and R. J. Braddock, entitled "Florida Citrus Oil", and published in December 1971 by Agricultural Experiment Station, Institute of Foods and Agricultural Sciences, University of Florida, Gainesville, Fla.

The d-limonene employed in the compositions of the present invention can be of a relatively impure grade without causing significant degradation of the solvent capabilities of the resultant solution. However, some researchers believe that the presence of significant amounts of impurities in d-limonene speeds the formation of decomposition products to which the skin of some people's hands may be sensitive, and so more refined grades of d-limonene are preferable from this standpoint. Also, the more highly refined grades of d-limonene lack the citrus odor which is characteristic of the material, but the odor itself is generally not considered offensive.

The final component of the solvent composition is the "coupler" which permits the two, dissimilar solvent portions to exist together in a homogeneous, single phase solution. Without the inclusion of such a "coupler" (or "coupling agent"), it is simply not possible to get the polar carbonate and non-polar terpene to stay in the solution together; these compounds very strongly tend to "bead" when any attempt is made to mix them together in the absence of a coupler, and they will quickly separate out from one another, even after vigorous mixing and agitation.

A characteristic of effective coupling agents has been found to be that they exhibit both polar and non-polar characteristics in the same molecule; in other words, each molecule is part polar and part non-polar, so as to essentially provide a link between the polar and non-polar molecules in the solution. In this regard, it has been found that small-chained, non-ionic surfactants are suitable for use as coupling agents in the solvent composition of the present invention, and that glycol ethers and their acetates are preferable for this purpose. Suitable glycol ethers and their acetates have the structure:

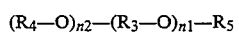

wherein $n_1$ and $n_2$ are the numerals 1–3, and wherein $R_3$ is a hydrocarbon radial having 2–3 carbon atoms, $R_4$ is a hydrogen or a hydrocarbon radical having 1–4 carbon atoms, and $R_5$ is a hydrogen or a hydrocarbon radial having 1–4 carbon atoms.

Both ethylene- and propylene-based glycol ethers have been found particularly effective as coupling agents for the solvent composition of the present invention, and suitable examples of these two families are listed below:

Propylene-Based Glycol Ethers

Propylene Glycol
Methyl Ether
Dipropylene Glycol
Methyl Ether
Tripropylene Glycol
Methyl Ether
Propylene Glycol
Methyl Ether Acetate
Dipropylene Glycol
Methyl Ether Acetate
Propylene Glycol
n-Butyl Ether
Propylene Glycol
n-Butyl Ether
Propylene Glycol
t-Butyl Ether Ethylene-Based Glycol Ethers Ethylene Glycol
n-Butyl Ether
Diethylene Glycol
n-Butyl Ether
Triethylene Glycol
n-Butyl Ether Diethylene Glycol
Methyl Ether For reasons essentially similar to those which were discussed above with respect to the advantages of propylene carbonate relative to ethylene carbonate, the propylene-based glycol ethers are generally preferred over the glycol-based glycol ethers, since the propylene-based compounds degrade safely in a living system. In particular (as is also the case with propylene carbonate), the main metabolite of the propylene-based glycol ethers is propylene glycol, which is used extensively in cosmetics and as a food additive. Most preferred for use in the composition of the present invention is tripropylene glycol methyl ether, because of its very low vapor pressure. The vapor pressure of tripropylene glycol methyl ether is lower than that of either the propylene carbonates of the d-limonene, with the result that the glycol ether is the last to evaporate off; this ensures that the coupling agent will always be present in the composition so as to prevent the carbonate and terpene from separating out, this relationship being maintained regardless of any evaporative losses which may occur over a long period of use. The ethylene-based glycol ethers, by contrast, while they also biodegrade well in the environment, are less desirable from the standpoint of personnel exposure, inasmuch as some are readily absorbed through the skin and do not degrade as safely within living systems.

EXAMPLE FORMULATIONS

The novel solvent compositions of the present invention will be more fully understood from a consideration of the following examples, which illustrate preferred embodiments. It is to be understood, however, that these examples are given by way of illustration and not of limitation.

EXAMPLE I

A solvent composition was prepared by simple mixing of the following, preferably always maintaining a sufficient amount of the glycol ether in the solution to prevent beading of the other two components:

|     | Component | % (By Weight) |
| --- | --- | --- |
| (a) | Propylene Carbonate (CAS #108-32-7, 1,3-Dioxolan-2-one methyl) | 25 |
| (b) | d-Limonene (CAS #5989-27-5, 4-isopropenyl-1-methylcyclo hexene) | 17 |
| (c) | Tripropylene Glycol Methyl Ether (CAS #25498-49-1 | 58 |

This particular formulation (which has been designated "EP921") has widespread applicability, and has been found particularly effective for use in cleaning up guns and lines have been used for applying paint and other coatings, and also for the deglazing of rollers which are used in offset printing.

EXAMPLE II

A solvent composition was prepared containing:

|     | Component | % (By Weight) |
| --- | --- | --- |
| (a) | Propylene Carbonate (CAS #108-32-7, 1,3-Dioxolan-2-one, methyl) | 60 |
| (b) | d-Limonene (CAS #5989-27-5, 4-isopropenyl-1-methylcyclo hexene) | 1 (or less) |
| (c) | Tripropylene Glycol Methyl Ether (CAS #25498-49-1) | 39 |

This formulation is somewhat more specific in its applicability than that of Example I, this having been found useful primarily for the cleaning and reclamation of silkscreens, and in the clean-up of aluma-printing surfaces and equipment. This is the result of reducing the amount of d-limonene to 1% or less, which tends to enhance the polar aspect of the solvent mixture. Nevertheless, it has been found that, even at these relatively low levels (e.g., 0.5–1%), the d-limonene enables the synergism to be developed with the propylene carbonate such that the effective solvent action of this mixture is significantly greater than that which would be exhibited by the mixture if it contained only the propylene carbonate and the glycol ether.

Other exemplary formulations in accordance with the present invention may be prepared as follows:

EXAMPLE III

|     |     | by weight |
| --- | --- | --- |
| (a) | Propylene Carbonate | 36.2% |
| (b) | d-limonene | 7.4% |
| (c) | Tripropylene Glycol Methyl Ether | 56.4% |

EXAMPLE IV

|     |     | by weight |
| --- | --- | --- |
| (a) | Propylene Carbonate | 40.3% |
| (b) | d-limonene | 4% |
| (c) | Propylene Glycol Ether Acetate | 55.7%— |

The compositions provided by the exemplary formulations given above have been found to be highly effective solvents which are non-corrosive to metal substrates. The design of EP921 creates material which mimics the solubility parameters and, more importantly, creates near congruence with the solubility vector, of methyl ethyl ketone. The radii of interaction have been artificially expanded, and an enhances spectrum of wettability created, so as to enlarge the scope of paints and resins which can be cleaned with this material. However, in contrast with MEK, the material is safe for human exposure, and poses minimal waste disposal problems. The blends were consequently found to be safe and effective substitutes to replace MEK and MEK/toluene blends, especially for paint gun and line clean-up, and for silkscreening applications. It was also found that the EP921 formulation provides an effective replacement for the methylene chloride, toluene, and 1,1,1 trichloro-ethane blends which have traditionally been used in offset printing processes to deglaze the ink and metering rollers. On a more commonplace level, this solvent composition has been found to produce good results when used for the removal of glues and adhesives, as a mild paint remover, as a grease and oil remover, and for removal of felt marker markings and machinist's blue dye, thus demonstrating its effectiveness as a general purpose cleaner. Final rinsing to remove residual solvent is easily achieved with warm water, followed by an air blast to dry the part if necessary.

Analytical Results and Field Testing

A thorough product analysis and extensive field testing was conducted with respect to the exemplary solvent compositions having the formulations set forth in Examples I and II above. For example, EP921 (i.e., the formulation of Example I above) has been found to exhibit the following relevant characteristics:

| TECHNICAL INFORMATION | |
|---|---|
| Boiling Point: | >340° F. |
| Vapor Pressure (MMHG) | .2 at 25° C. |
| Vapor Density Air = 1 | 4.7 |
| Specific Gravity H$_2$O = 1 | .98 |
| % Volatile by weight | 17% |
| Volatile component | 167 grams per liter |
| Overall Solubility Parameter | 9.3 |
| London Dispersion Forces | 8.1 |
| Polarity | 3.2 |
| Hydrogen Bonding | 3.2 |

A review of the components contained in these formulations reveals that these lie outside of the RCRA (Resource Conservation And Recovery Act of 1976) Hazardous Waste Regulations, and so the very expensive waste disposal costs which are associated with MEK and similarly hazardous compounds are avoided; similarly, none of the components are listed under CERCLA (Comprehensive Environmental Response, Compensation, and Liability Act of 1980—"Superfund"). Furthermore, none of these components (assuming use of the preferred propylene-based components) are listed in SARA Title III, §302 or 313, and so are not considered toxic chemicals in the workplace. Still further, the low Volatile Organic Compounds (VOC) content and high flash point of these compositions contribute to making them ideal solvents for functioning within the modern regulatory climate. The very low vapor pressure (see table above) minimizes evaporative losses to the atmosphere, and, in fact, the emission limitations which are thus inherent in this formulation may qualify it as a Best Available Control Technology (BACT) for regulatory purposes, by comparison with known formulations using vapor collection systems. For example, even without the use of a vapor collection system, the losses to the atmosphere from the EP921 formulation compare very favorably with the use of MEK in conjunction with a vapor collection system having 99.7% efficiency (which efficiency would be difficult to attain in practice).

These advantages were confirmed by theoretical analyses of the solvent compositions, as well as by extensive field testing. As regards the theoretical analysis, this was conducted using two models, the first assuming a closed system and the second assuming an open system, with real world performance expected to fall somewhere between the results derived from these two models. The first model assumed that equilibrium had been reached between a liquid and vapor phase in an enclosed environment. Under this condition, the amount of material lost to the gas phase corresponds to the vapor pressure of each of the two chemicals being compared. The vapor pressure of MEK was determined to be approximately 70 mmHg, while (as was noted in the table above) the vapor pressure of the EP921 formulation of the present invention was found to be 0.2 mmHg. Based upon these determinations, and assuming that both materials exhibit similar vapor and liquid behaviors, it was calculated that the amount of MEK lost to evaporation would be roughly 350 times greater than that of the EP921 solvent.

To then compare the two liquids in a non-equilibrium open system, it was necessary to use evaporation rates in the calculations. The evaporation rate given for MEK ranges from 3.8 to 5.7 (butyl acetate=1.0), whereas the evaporation rate for the EP921 version of the solvent of the present invention was calculated to be less than 0.02. In order to be on the conservative side, the least favorable numbers relative to the EP921 solvent formulation were used in making this calculation; accordingly, MEK is assumed to have an evaporation rate of 3.8, and EP921 was assumed to have an evaporation rate of 0.02. From these evaporation rates, it was determined that it would take the EP921 solvent 190 times longer than MEK to evaporate the same quantity of liquids. In other words, if it took 30 minutes to lose 90% of the MEK from an open container, it would theoretically take 4 days to lose the same amount of EP921.

Of course, actual consumption in real world operations is influenced by various other factors besides vapor pressures and theoretical evaporation rates. Actual consumption creates are significantly effected by drag-out, agitation longevity of cleaning power, reclamation efforts, and individual site practices. Accordingly, two site tests were carried out to determine the performance of the solvent compositions of the present invention relative to that of MEK.

The first field test was conducted using the "EP921" solvent given by Example I above. This testing was conducted in a large pulp and paper mill having 17 full-time painters engaged in on-site maintenance painting. Prior to adopting the EP921 solvent as a substitute for MEK in cleaning painting equipment, this facility routinely consumed twelve 55-gallon drums of MEK per month for this purpose. Since adopting the low-vapor pressure EP921 solvent as a replacement for the MEK, consumption (of the EP921) has fallen to between two and four drums per month. Inasmuch as this facility did not practice any reclamation or life-extending procedures with respect to the solvent during this test, this usage difference is most probably entirely attributable to the differences in cleaning power and evaporation rate between EP921 and the MEK which it has replaced.

Similarly, site testing was carried out using the solvent composition which is set forth in Example II above. This formulation, which there is relatively low amount of d-limonene, is especially well-suited for use in cleaning and reclamation of silkscreens, and so has been assigned the designation of "Silkscreen B".

The site selected was a facility using an aluma printing process to screen permanent printing on aluminum sheeting. This shop's prior consumption was 7000 pounds of MEK per month, just to support this process. After switching to the low-vapor pressure solvent in accordance with the present invention, the site's consumption of solvent diminished to 1600 pounds per month. Simultaneously, a several-fold increase in productivity was achieved: with the MEK process, productivity was 1250 parts per week; after switching the process to the "Silkscreen B" solvent composition of the present invention, productivity increased to 4000 parts per week. The lower productivity experienced when using MEK appears to have been related to the frequent need to shut the system down and replace the dirty MEK; "Silkscreen B" lasts far longer in this process, resulting in far fewer change-outs and much less down time.

As an additional benefit of the low vapor pressure and evaporation rates which are exhibited by the solvent of the present invention relative to MEK, it has been found that this greatly reduces the likelihood that the solubilized material will re-adhere to or re-deposit on the cleaned surface to evaporative losses of the solvent.

The present invention thus provides a liquid solvent mixture which is low in toxicity, and presents an effective and environmentally beneficial alternative to conventional cleaning solvents like MEK and methylene chloride. The preferred mixture of propylene carbonate, d-limonene, and tripropylene glycol methyl ether out-performs most conventional solvents, without harming the substrate, be it ceramic, glass, metal, or plastic. The field experience with the solvent mixture of the present invention demonstrated that this is not only a safe and economical solvent, especially from the standpoint of regulatory requirements, but that it is a surprisingly effective solvent for many industrial cleaning applications, and that its longevity in use increases its economic advantages.

The solvent of the present invention can include other additives to address specific cleaning problems, and provide further improved solvent effect for particular applications. The selection of the particular additives and the amounts used should be consistent with the objective of providing a solvent with a low-vapor pressure which is essentially non-toxic and safe in terms of environmental hazards. For example, thickening agents may be added to the solution if so desired.

One of ordinary skill, after reading the foregoing specification and the appended claims, will be able to effect various changes, substitutions of equivalents, and other alternatives without departing from the broad, inventive concepts discussed herein. Accordingly, the claims should be construed broadly in light of the description so as to include all descried embodiments and their equivalents, and should only be limited as required by the relevant prior art.

What is claimed is:

1. A low toxicity solvent composition consisting essentially of:
    (a) propylene carbonate in an amount from about 25% to about 60% by weight of said composition;
    (b) d-limonene in an amount from about 1% to about 20% by weight of said composition; and
    (c) tripropylene glycol methyl ether in an amount from about 40% to about 60% by weight of said composition.

2. A low toxicity general purpose solvent composition consisting essentially of:
    (a) propylene carbonate in an amount of about 25% by weight of said composition;
    (b) d-limonene in an amount of about 17% by weight of said composition; and
    (c) tripropylene glycol methyl ether in an amount of about 58% by weight of said composition.

3. A low toxicity solvent composition consisting essentially of:
    (a) propylene carbonate in an amount of about 60% by weight of said composition;
    (b) d-limonene in an amount of about 1% of said composition; and
    (c) tripropylene glycol methyl ether in an amount about 39% of said composition.

* * * * *